United States Patent [19]
Klaue

[11] Patent Number: 4,513,744
[45] Date of Patent: Apr. 30, 1985

[54] SURGICAL COMPRESSION PLATE

[75] Inventor: Kaj Klaue, Sierre, Switzerland

[73] Assignee: Synthes AG, Chur, Switzerland

[21] Appl. No.: 441,633

[22] Filed: Nov. 15, 1982

Related U.S. Application Data

[63] Continuation-in-part of Ser. No. 358,389, Mar. 15, 1982.

[30] Foreign Application Priority Data

Mar. 16, 1981 [CH] Switzerland .................. 17731/81

[51] Int. Cl.³ .............................................. A61F 5/04
[52] U.S. Cl. ............................... 128/92 D; 128/92 B
[58] Field of Search .................. 128/92 D, 92 R, 92 B

[56] References Cited

U.S. PATENT DOCUMENTS 3,552,389  1/1971  Allgower et al. ............... 128/92 D
3,779,240 12/1973  Kondo .............................. 128/92 D
4,219,015  8/1980  Steinemann ..................... 128/92 D
4,408,601 10/1983  Wenk .............................. 128/92 D

FOREIGN PATENT DOCUMENTS 1505513 11/1967 France ............................. 128/92 D
1153090  5/1969 United Kingdom ............ 128/92 D Primary Examiner—C. Fred Rosenbaum
Assistant Examiner—C. W. Shedd
Attorney, Agent, or Firm—Davis Hoxie Faithfull & Hapgood

[57] ABSTRACT

A surgical compression plate is provided with at least one elongated screw hole with a sloping camming surface that bows outwardly to provide a constant torque until the screw is seated or a torque that increases gradually and then diminishes until the screw is seated, with a sudden increase in torque on seating, thereby to advise the surgeon that the screw has been seated.

9 Claims, 10 Drawing Figures

SURGICAL COMPRESSION PLATE

This application is a continuation-in-part of my copending application Ser. No. 358,389 filed Mar. 15, 1982.

This invention relates to compression plates for use in reducing bone fractures. In particular it relates to an improved compression plate which is easier for the surgeon to use and reduces the danger of placing excessive load on the screws used to secure the plate.

The compression plate described and claimed in U.S. Pat. No. Re 28,841 has one or more elongated holes or slots for receiving screws, preferably round headed screws, in which the sides of the slots are sloped inwardly and downwardly in cylindrical configuration so that when the screw is advanced into the bone the bone fragments are brought together by a camming action and then compressed. Further description of this and other styles of compression plates may be found in the following references:

Allgower et al., *The Dynamic Compression Plate DCP*, Berlin/Heidelberg/New York, Springer-Verlag (1973)

Mueller et al., *Manual der Osteosynthese (AO Technik)*, 2nd Edition, Berlin/Heidelberg/New York, Spring Verlag (1977)

Swiss Patent Nos:
468 824
600 862
611 147
613 616
613 858

In using compression plates of this general type one may identify three steps in the reduction of the fracture, viz:

A. Longitudinal displacement, in which the fragments are brought into contact
B. Compression, in which the fragments are pressed together
C. Fixation of the plate, the point at which the screw is seated in the hole in the plate.

With prior designs, the screw head moved down into the plate slot in a more or less straight line, i.e., the locus of the successive positions of the center of the screw head as the screw was advanced into the bone was substantially a straight line. Because the resistance to the screw varied as the screw advanced, the torque exerted on the screw increased as a more or less smooth curve. One difficulty with this was that the surgeon inserting the screw could not be certain, from the resistance encountered, when the screw was fully seated. As a result it occasionally happened that screws would be bent or deformed.

In accordance with the present invention these difficulties are avoided by providing a compression plate having elongated holes or slots whose side surfaces are sloped inwardly and downwardly with variable slope, bowing outwardly in the direction of the hole opening or longitudinal screw displacement, the slope being designed to maintain constant torque or gradually increasing torque during the longitudinal displacement and compression stages, with a sudden, abrupt increase in torque as the screw is seated; or, preferably, with a diminution of the torque toward the end of the compression stage followed by a sudden increase as the screw is seated.

The invention will be further described with reference to the accompanying drawings in which.

Figure 1A:
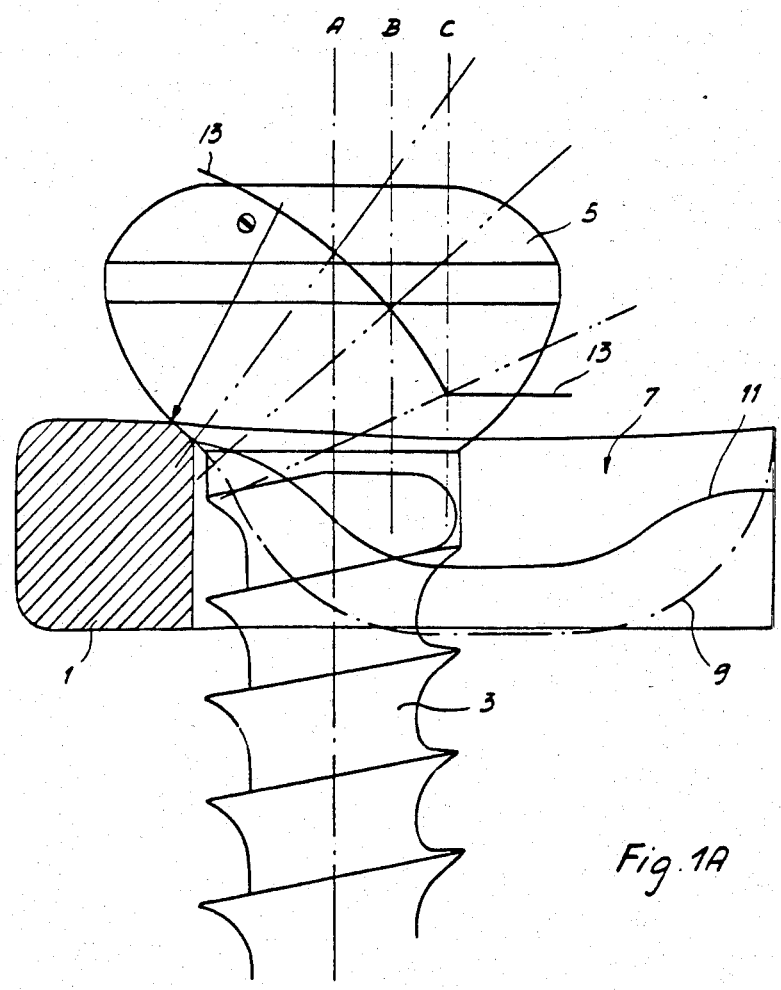
FIGS. 1A to 1C are views taken in side elevation and partly in vertical section of a plate according to the invention, together with a screw in various positions corresponding to the longitudinal displacement, compression and seating stages.
Figure 1B:
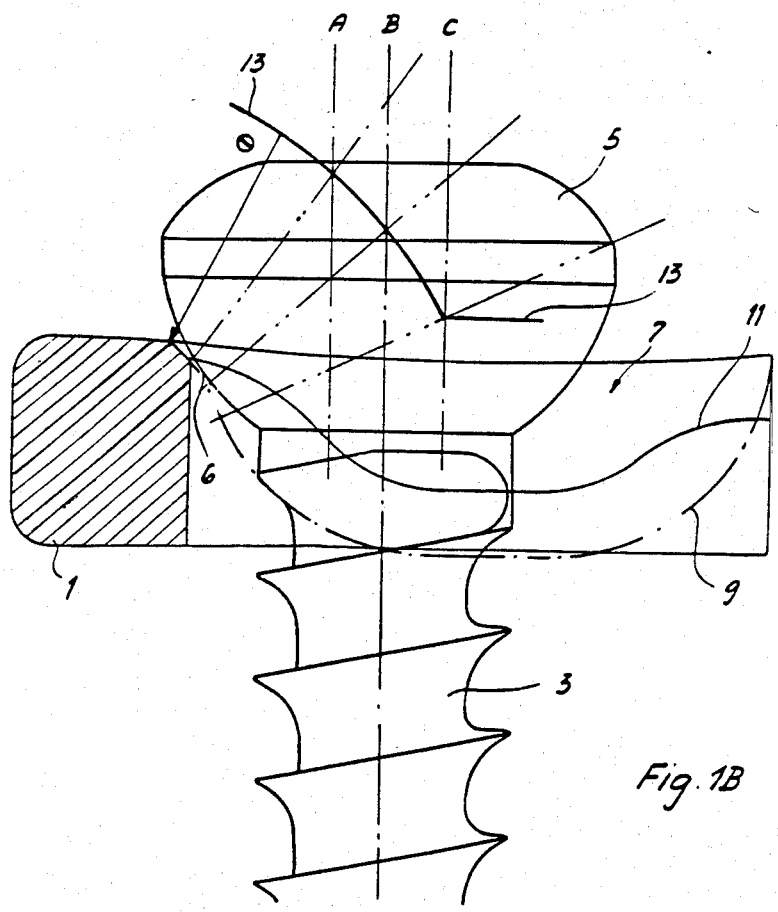
Figure 1C:
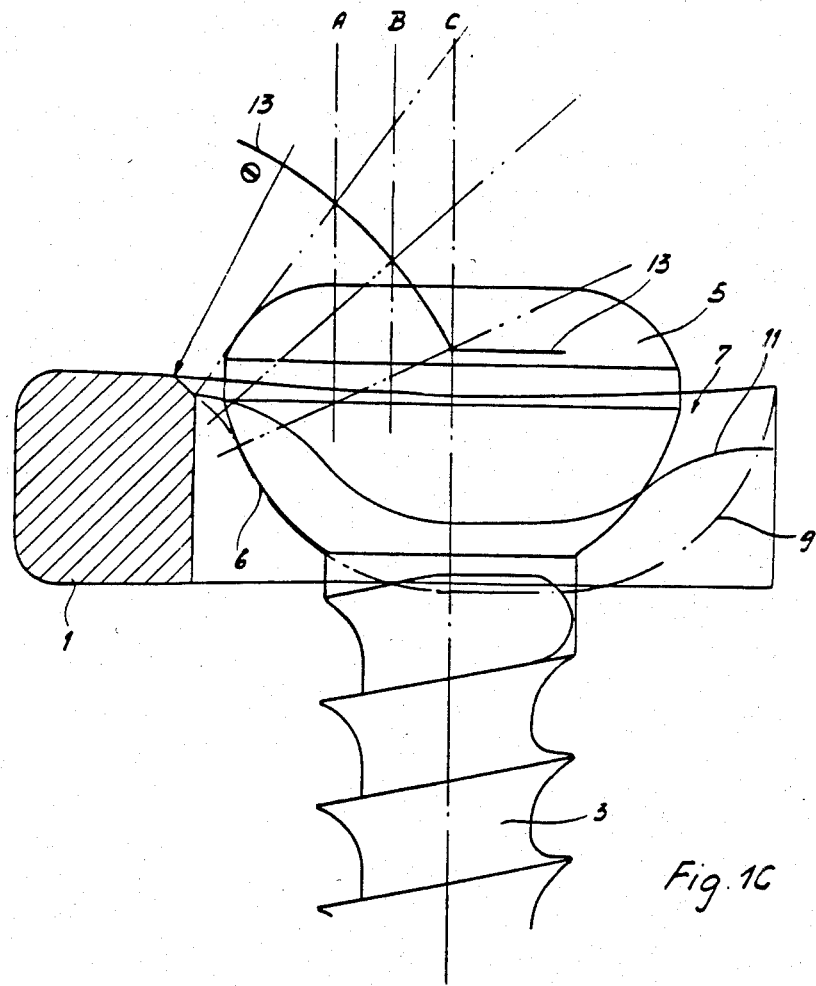

Referring to FIGS. 1A to 1C, a system according to the invention comprises a plate 1 having an elongated hole or slot 7 and a screw 3 having a head 5 which is preferably, but not necessarily hemispheric in shape. The side walls of the slot are sloped inwardly and downwardly to provide a surface 11 against which the bottom surface of the screw bears as it is advanced vertically downwardly into the bone (not shown). The effect of this plate/screw contact is to move the screw longitudinally along the axis of the plate. FIG. 1A shows the screw at the beginning of its travel. FIG. 1B shows the screw advanced downwardly into the bone and displaced longitudinally to the right. FIG. 1C shows the screw seated in the slot. It will be observed that the screw in FIG. 1C can still have longitudinal displacement. Thus the effect of other screws in the same plate can be provided for.

In accordance with the invention, the travel of the screw longitudinally is not a straight line but is a combination of intersecting straight lines or a curve which bows outwardly in the direction of longitudinal displacement. This can be observed from FIGS. 1A–1C where the locus of a point at the center of the screw head, as displacement occurs, is shown by line 13. As depicted in FIGS. 1A–1C the slope of curve 13 is intended as illustrative rather than definitive.

Figure 2:
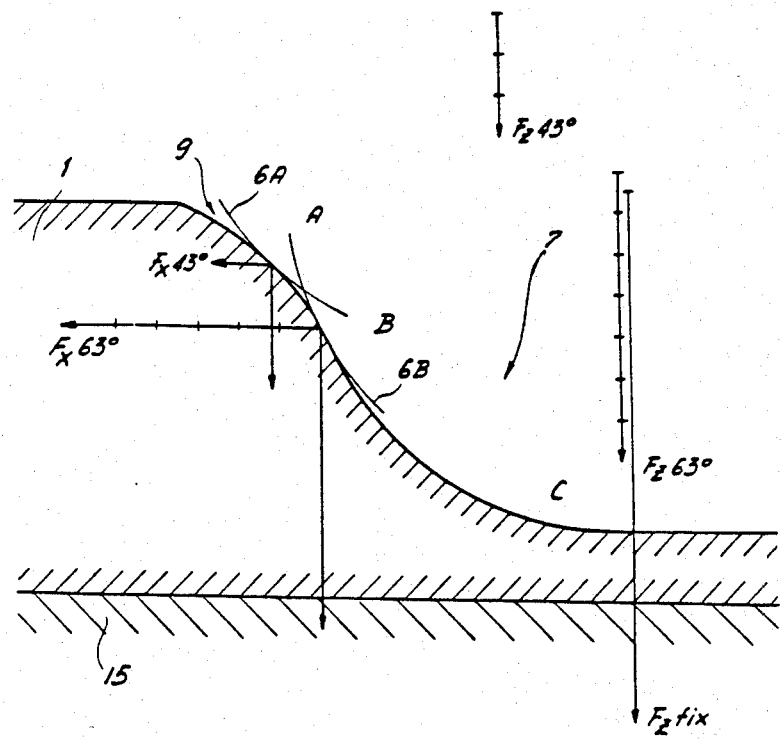
FIG. 2 is a curve of the points of tangency of a spherical screw head and the wall of the elongated hole or slot in a plate according to the invention.
Figure 3:
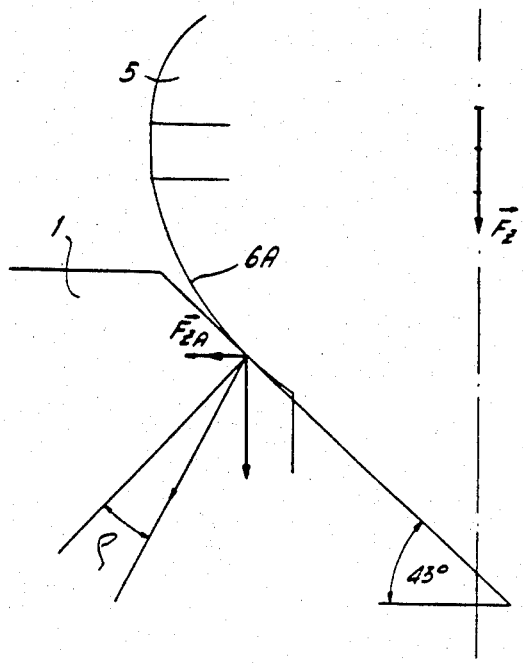
FIG. 3 is a diagram showing the relationship of forces in the longitudinal displacement phase with a system according to the invention.
Figure 4:
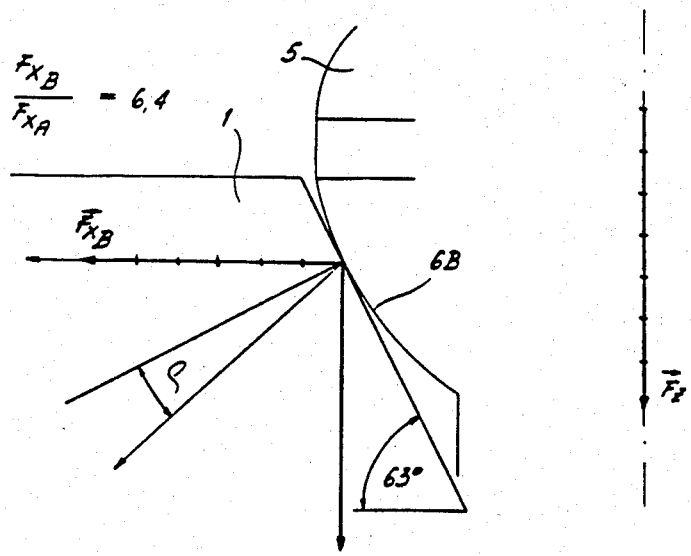
FIG. 4 is a diagram showing the relationship of forces toward the end of the compression phase with a system according to the invention.
Figure 5:
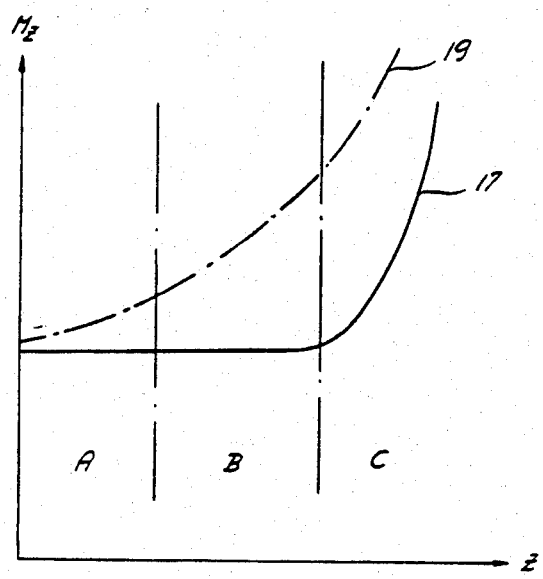
FIG. 5 is a graph of torque and displacement comparing a plate according to the invention with a more conventional plate.

FIG. 2 is a graph of the points of contact of the plate and screw in a vertical plane through the axis of the plate. As shown in FIG. 2 in phase A the slope of the curve at a point of contact is about 43°; in phase B it increases and at the point shown is 63°. The result of this in terms of forces in the two major directions is shown in FIGS. 3 and 4. In this particular case the relationship between $F_{XA}$, the force in the X direction in phase A, and $F_{XB}$, the force in the X direction in phase B is $$F_{XA}/F_{XA} = 6.4.$$

In FIGS. 3 and 4, is a function of the friction between screw and plate.

Figure 6:
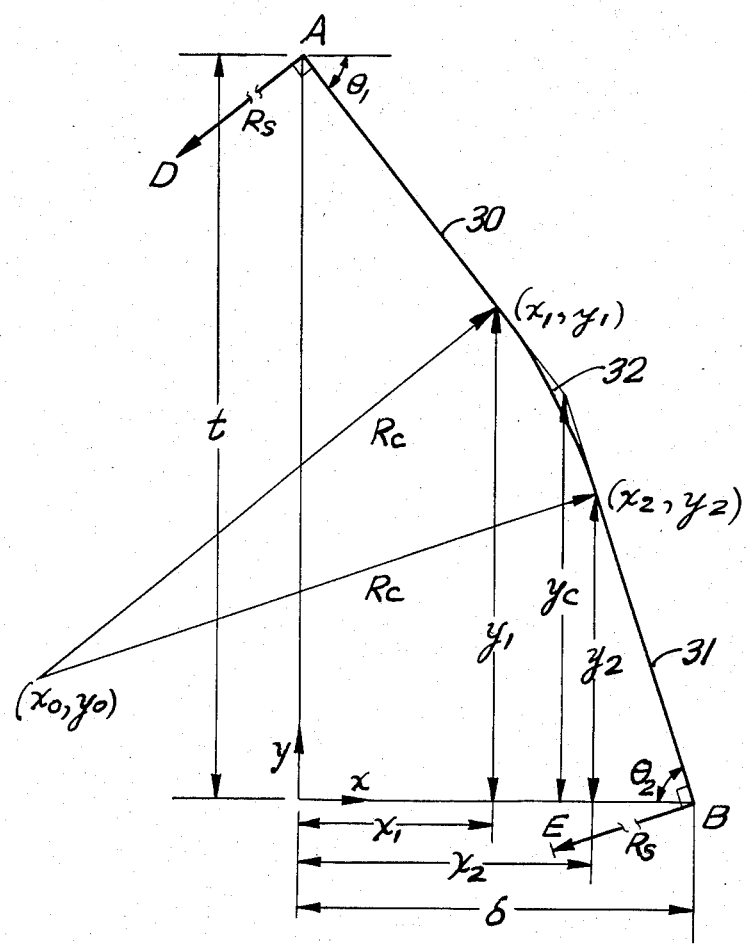
FIG. 6 is a diagram representing, in a simplified way, the locus of the center of a screw head used with a plate of preferred design according to the invention.

In designing a plate according to the invention the movement of the screw head can be considered in terms of two straight lines of different slope. This is illustrated in FIG. 6 where the screw moves from the initial point of contact A along an upper path 30 which makes an angle $\theta_1$ with the horizontal to a point $(X_1, Y_1)$. At the lower section of its travel, from a point $(X_2, Y_2)$ to point B, the path 31 of the screw head is more nearly vertical, making an angle $\theta_2$ with the horizontal. In some instances the points $(X_1, Y_1)$ and $(X_2, X_2)$ may coincide, i.e., the travel may be two intersecting straight lines. However, in many instances it will be impractical for the two paths to meet at an angle, and points $(X_1, Y_1)$ and $(X_2, Y_2)$ will be joined by a curve 32 which is preferably the arc of a circle having a radius Rc. Useful values for Rc may be determined by the following relationship, where t and $\delta$ are the total vertical and maximum horizontal screw travels, respectively.

$$Rc = [(t+\delta)/2]$$

It is to be understood, however, that it is not critical for Rc to have a value conforming to this relationship.

A complete description of the screw travel (locus of the center of the screw head) can be expressed mathematically as follows:

For $0 \leq X \leq X_1$
$\quad Y = -\tan\theta_1 X + t$
For $X_1 \leq X \leq X_2$
$\quad (X - X_0)^2 + (Y - Y_0)^2 = Rc^2$
For $X_2 \leq X \leq \delta$
$\quad Y = -\tan\theta_2 (X - \delta)$ $$X_0 = \frac{Rc(\cos\theta_2 - \cos\theta_1) + \delta \cdot \sin\theta_2 \cdot \cos\theta_1 - t \cdot \cos\theta_1 \cdot \cos\theta_2}{\cos\theta_1 \cdot \cos\theta_2 \cdot (\tan\theta_2 - \tan\theta_1)}$$

$$Y_0 = \frac{t \cdot \cos\theta_1 - Rc - X_0 \cdot \sin\theta_1}{\cos\theta_1}$$

$$X_1 = \frac{t \cdot \tan\theta_1 - Y_0 \cdot \tan\theta_1 + X_0}{\tan^2\theta_1 + 1}$$

$$X_2 = \frac{\delta \cdot \tan^2\theta_2 - Y_0 \cdot \tan\theta_2 + X_0}{\tan^2\theta_2 + 1}$$

In order that the surgeon may have the clearest possible indication that the screw has been fully inserted, it is desirable that the torque just prior to the seating phase be minimized to provide a constrast with the increase in torque observed at seating. Hence, it is desirable that the slope angle of the terminal section of the slot surface be maximized. Given a few basic conditions maximum values for the slope of the terminal section and the minimum initial angle can be calculated by trial and error using any conventional computer.

The chief constraints to be considered are minimum and maximum plate thickness, minimum and maximum horizontal travel and the minimum vertical travel for the terminal portion of the screw travel. The plate thickness is obviously determined by the particular application, but typically is from 3.6 to 3.9 mm. Horizontal travel also depends on the purpose but is typically 1–2 mm. The minimum vertical travel will depend on screw size and pitch but should conform to at least 270° of screw rotation, or in general at least 1.27 mm.

If desired, a more refined determination can be made, taking additional constraints into account. One of these is the ratio, travel length (of the center of the screw head)/contact length, which is a measure of the plate abrasion. Referring to FIG. 6, points D and E represent the initial and final contact points (or contact lines) between the plate and the screw head, $R_s$ being the radius of the screw head (shown greatly foreshortened in FIG. 6). To a first approximation, the ratio referred to, designated FR, is:

$$FR = \frac{\sqrt{t^2 + \delta^2}}{|DE|}$$

where DE is the distance between D and E, t is the total vertical travel, and $\delta$ is the maximum horizontal travel.

It has been found experimentally that this ratio should be approximately 2.0.

Another constraint which may be taken into account is the so-called corner sharpness, the abruptness of transition from the initial angle, to the terminal angle. To estimate this factor, the travel path is represented by a third order polynomial.

$$Y = C_1 X^3 + C_2 X^2 + C_3 X + C_4$$

The constants are solved for using the initial and final points and slopes:
 1. When $X=0$, $Y=t$
 2. When $X=\delta$, $Y=0$
 3. At $X=0$, $dy/dx = -\tan\theta_1$
 4. At $X=\delta$, $dy/dx = -\tan\theta_2$ The "corner sharpness" is then the second derivative of Y with respect to X, $$d^2y/dx^2 = (\tan\theta_1 - \tan\theta_2)$$

To allow for the effect of the area in which the transition occurs, the product $(\delta \cdot t)^{-1}$ is taken with the above, to give the final factor, designated SH:

$$SH = \frac{1}{\delta \cdot t} (\tan\theta_2 - \tan\theta_1)$$

A value of 0.55 or less has been found acceptable for this factor.

Figure 7:
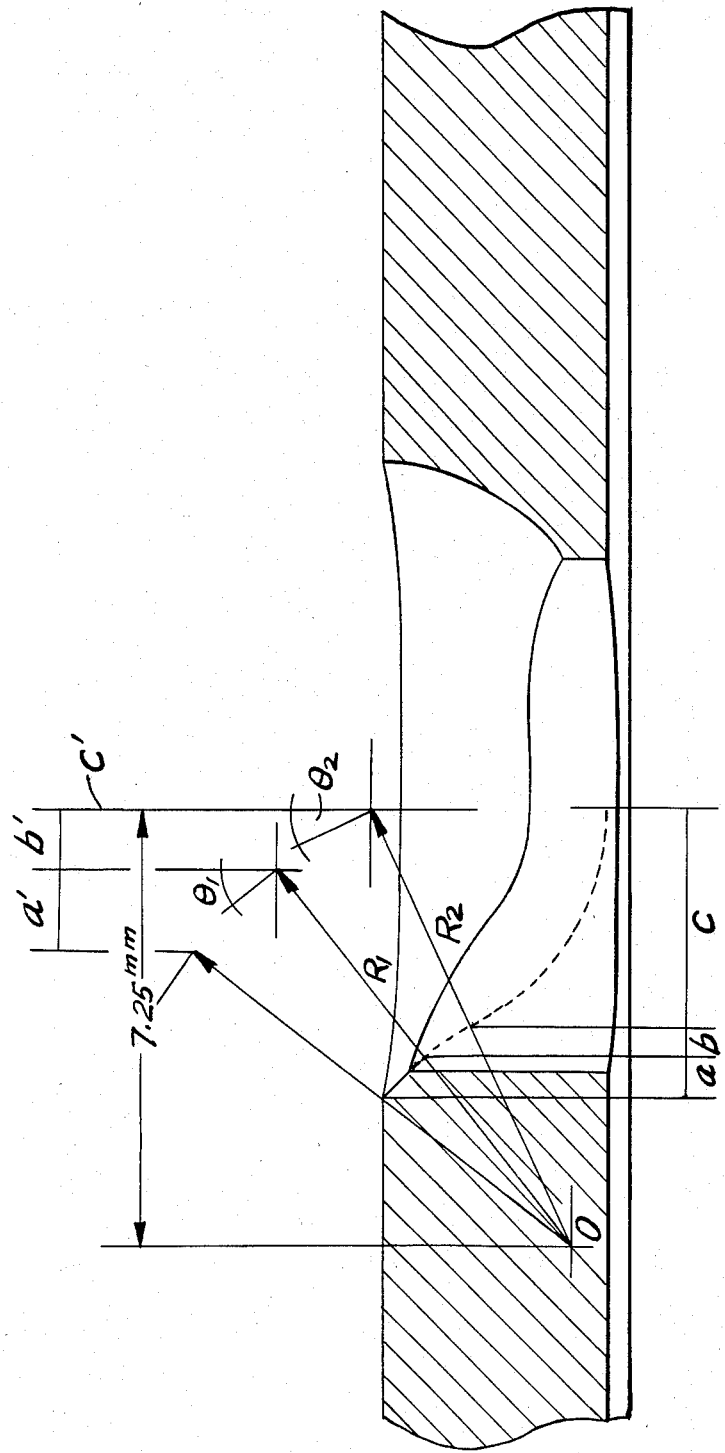
FIG. 7 is a diagrammatic view of a plate according to the invention, illustrating the initial and final positions of the screw.

The following program (Fortran 77) has been developed for obtaining the maximum final angle and minimum initial angle and the other parameters of the system, namely, the location of the screw head at the initial and final positions relative to a chosen origin $(R_1, R_2)$, the total horizontal travel, the total vertical travel, the vertical travel in the steep portion (YC), the FR factor, the SH factor and the plate thickness, give limiting values for horizontal travel (minimum and maximum) minimum vertical travel for the steep portion, maximum FR, maximum SH, and minimum and maximum plate thickness. Referring to FIG. 7, the radii $R_1$ and $R_2$ at the initial and final positions of the screw are taken from an arbitrary origin at the level of the bottom of the screw head when fully seated and at a point 7.25 mm from the center of the screw when fully seated. Any other convenient origin could equally well be chosen. Distances a, b and c represent the longitudinal distances along the axis of the plate corresponding to displacement, compression and seating. Distances a' and b' represent travel of the center of the screwhead on plates a and b. The point c' is the position of the center of the screwhead when the screwhead is seated.

```
C    *****************************************************************
C    *                                                               *
C    *                    REFERENCES:                                *
C    *                                                               *
C    *    PTHIK:  plate thickness                                    *
C    *    PTMIN:  minimum plate thickness                            *
C    *    PTMAX:  maximum     "       "                              *
C    *      DEL:  total horizontal screw travel                      *
C    *   DELMIN:  minimum <DEL>                                      *
C    *   DELMAX:  maximum <DEL>                                      *
C    *       YC:  vertical screw travel in final (steep)             *
C    *            portion of the curve                               *
C    *    YCMIN:  minimum <YC>                                       *
C    *        T:  total vertical screw travel                        *
C    *     FRIK:  screw travel length relative to the                *
C    *            plate/screw contact length (a measure of           *
C    *            plate abrasion)                                    *
C    *    FRMAX:  maximum <FRIK>                                     *
C    *    SHARP:  a measure of the sharpness of the corner           *
C    *            required for the screw travel                      *
C    *    SHMAX:  maximum <SHARP>                                    *
C    *    THET1:  initial slope of the screw travel                  *
C    *    THET2:  final slope of the screw travel                    *
C    *            (both angles are relative to the long              *
C    *             axis of the plate)                                *
C    *   TH2MIN:  minimum final slope                                *
C    *       R1:  radius of curvature for the formation of           *
C    *            the initial slope                                  *
C    *       R2:  radius of curvature for the formation of           *
C    *            the final slope                                    *
C    *                                                               *
C    *****************************************************************
C
C    *** INITILIZE ***
C
      CHARACTER REP*1,FILE*15,LINE*80
      PTMIN=3.6
      PTMAX=3.9
      DELMIN=1.0
      DELMAX=2.0
      YCMIN=1.275
      FRMAX=1/0.40
      SHMAX=0.55
      PI=3.141592653589
      DR=2*PI/360
      RD=1/DR
      TH2MIN=30.0*DR
      I=1
10    WRITE(6,20)
20    FORMAT(/' ENTER FILE NAME FOR OUTPUT DATA: ',$)
      READ(5,30,ERR=10)FILE
30    FORMAT(A)
      OPEN(UNIT=1,NAME=FILE,TYPE='NEW',ERR=10)
C
C    *** CHANGE LIMITS IF DESIRED ***
C
100   WRITE(6,200)DELMIN,DELMAX,YCMIN,FRMAX,SHMAX,PTMIN,PTMAX
200   FORMAT(/'         THESE ARE THE LIMITING VALUES:'
     1//5X' 1) DELMIN =',F6.2,/5X'    2) DELMAX =',F6.2,
     2/ 5X' 3) YCMIN  =',F6.2,/5X'    4) FRMAX  =',F6.2,
     3/ 5X' 5) SHMAX  =',F6.2,/5X'    6) PTMIN  =',F6.2,
     4/ 5X' 7) PTMAX  =',F6.2)
250   WRITE(6,300)
300   FORMAT(//' WOULD YOU LIKE TO CHANGE ANY OF THE LIMITS
     1 (Y OR N)? ',$)
      READ(5,400,ERR=250)REP
400   FORMAT(A)
      IF(REP.EQ.'N')GOTO 600
410   WRITE(6,450)
```

```
450     FORMAT(/' WHICH LIMIT (1 THROUGH 7)? ',$)
        READ(5,460,ERR=410)LMN
460     FORMAT(I)
465     WRITE(6,470)
470     FORMAT(' ENTER NEW VALUE (F6.2): ',$)
        READ(5,480,ERR=465)VALUE
480     FORMAT(F6.2)
        IF(LMN.EQ.1)GOTO 501
        IF(LMN.EQ.2)GOTO 502
        IF(LMN.EQ.3)GOTO 503
        IF(LMN.EQ.4)GOTO 504
        IF(LMN.EQ.5)GOTO 505
        IF(LMN.EQ.6)GOTO 506
        PTMAX=VALUE
        GOTO 100
501     DELMIN=VALUE
        GOTO 100
502     DELMAX=VALUE
        GOTO 100
503     YCMIN=VALUE
        GOTO 100
504     FRMAX=VALUE
        GOTO 100
505     SHMAX=VALUE
        GOTO 100
506     PTMIN=VALUE
        GOTO 100
600     WRITE(6,610)
610     FORMAT(/' CONTINUE OR STOP (C OR S)? '$)
        READ(5,400,ERR=600)REP
        IF(REP.EQ.'S')STOP
        WRITE(1,700)I
700     FORMAT(///' ************************** RUN NUMBER'I3
       1        ' **********************************'////)
        WRITE(1,200)DELMIN,DELMAX,YCMIN,FRMAX,SHMAX,PTMIN,PTMAX
C
C       *** BEGIN WITH MAXIMUM THET2 ***
C
900     THET2=85.1*DR
C
C       *** ENTER R1 AND R2 ***
C
1000    WRITE(6,1100)
1100    FORMAT(' ENTER R1 (F6.2): ',$)
        READ(5,480,ERR=1000)R1
1250    WRITE(6,1300)
1300    FORMAT(' ENTER R2 (F6.2): ',$)
        READ(5,480,ERR=1250)R2
        WRITE(6,1400)
1400    FORMAT(/' CALCULATING...')
C
C       *** BEGIN WITH MINIMUM THET1 ***
C
1500    THET1=30.0*DR
C
C       *** CALCULATE ALL GEOMETRIC PARAMETERS ***
C
1600    T=R1*COS(THET1)-R2*COS(THET2)
        DEL=R2*SIN(THET2)-R1*SIN(THET1)
        XD=-4.1*SIN(THET1)
        XE=DEL-4.1*SIN(THET2)
        YC=TAN(THET1)*((T-TAN(THET2)*DEL)/(TAN(THET2)-TAN(THET1)))+T
        YD=T-4.1*COS(THET1)
        YE=-4.1*COS(THET2)
        PTHIK=YD+4.0
        FRIC=1/((SQRT((XD-XE)**2+(YD-YE)**2))/(SQRT(T**2+DEL**2)))
        SHARP=ABS((TAN(THET1)-TAN(THET2))/(DEL*T))
```

```
C         *** CHECK IF THE FRICTION FACTOR IS WITHIN THE CONSTRAINTS.
C             IT IS PRIMARILY A FUNCTION OF R1 AND R2 ***
          IF(FRIC.LE.FRMAX)GOTO 1700
          WRITE(6,1650)FRIC,FRMAX
1650      FORMAT(/' FRICTION FACTOR ='F6.2,
         1/' <GREATER THAN'F6.2,'>, RESTART.')
          GOTO 100
C
C         *** CHECK THE OTHER FOUR CONSTRAINTS. IF THEY ARE ALL MET,
C             THEN THE LOOP CAN BE LEFT. OTHERWISE, THE INITIAL SLOPE

C             <THET1> IS INCREASED UNTIL EITHER <YCMIN> OR <DELMIN> BREAK
C             THE LOOP, WHEREUPON <THET2> MUST BE DECREASED, AND <THET1>
C             IS RESTARTED AT ITS MINIMUM VALUE ***
C
1700      IF(SHARP.GT.SHMAX)GOTO 1701
          IF(YC.LT.YCMIN)GOTO 1702
          IF(DEL.GT.DELMAX)GOTO 1701
          IF(DEL.LT.DELMIN)GOTO 1702
          IF(PTHIK.GT.PTMAX)GOTO 1701
          IF(PTHIK.LT.PTMIN)GOTO 1702
          GOTO 1709
C
C         *** INCREASE THET1 OR DECREASE THET2 AND RETURN THET1 TO
C             ITS MINIMUM VALUE ***
C
1701      THET1=THET1+(1.0*DR)
          IF(THET1.GE.THET2)GOTO 1702
          GOTO 1600
C
1702      THET2=THET2-(0.1*DR)
          IF(THET2.LT.TH2MIN)GOTO 4000
          GOTO 1500
C
C         *** WHEN ALL CONSTRAINTS ARE MET, RESULTS ARE PRINTED, WHICH
C             CORRESPOND TO THE MAXIMUM FINAL SLOPE AND THE MINIMUM
C             INITIAL SLOPE ***
C
1709      WRITE(6,1710)
          WRITE(1,1710)
1710      FORMAT(/'            ********* RESULTS: *********')
          WRITE(6,1720)THET2*RD,THET1*RD
          WRITE(1,1720)THET2*RD,THET1*RD
1720      FORMAT(//'        *** MAXIMUM FINAL SLOPE = 'F6.2' DEGREES ***'
         1//' FOR WHICH THE MINIMUM INITIAL SLOPE = 'F6.2' DEGREES')
          WRITE(6,1730)
          WRITE(1,1730)
1730      FORMAT(/'       AND HAS THE FOLLOWING PARAMETERS:')
          WRITE(6,1740)R1,R2,DEL,T,YC,FRIC,SHARP,PTHIK
          WRITE(1,1740)R1,R2,DEL,T,YC,FRIC,SHARP,PTHIK
1740      FORMAT(/10X'    R1 = 'F6.2,/10X'    R2 = 'F6.2,
         1   /10X'   DEL = 'F6.2,/10X'     T = 'F6.2,
         2   /10X'    YC = 'F6.2,/10X'  FRIC = 'F6.2,
         3   /10X' SHARP = 'F6.2,/10X' PTHIK = 'F6.2)
1750      WRITE(6,610)
          READ(5,400,ERR=1750)REP
          IF(REP.EQ.'S')GOTO 3190
          GOTO 2500
C
C         *** NOW THET1 IS INCREASED UNTIL ANY ONE OF THE CONSTRAINTS
C             ARE BROKEN, TO DETERMINE THE RANGE FOR THE INITIAL SLOPE
C             CORRESPONDING TO THE MAXIMUM FINAL SLOPE AS CALCULATED ***
```

```
2500      THET1=THET1+(0.01*DR)
          T=R1*COS(THET1)-R2*COS(THET2)
          DEL=R2*SIN(THET2)-R1*SIN(THET1)
          XD=-4.1*SIN(THET1)
          XE=DEL-4.1*SIN(THET2)
          YC=TAN(THET1)*((T-TAN(THET2)*DEL)/(TAN(THET2)-TAN(THET1)))+T

YD=T-4.1*COS(THET1)
          YE=-4.1*COS(THET2)
          PTHIK=YD+4.0
          SHARP=ABS((TAN(THET1)-TAN(THET2))/(DEL*T))
C
          IF(PTHIK.LE.PTMIN)GOTO 3000
          IF(YC.LE.YCMIN)GOTO 3000
          IF(DEL.LE.DELMIN)GOTO 3000
          IF(SHARP.GE.SHMAX)GOTO 3000
          GOTO 2500
C
C         *** UPPER LIMIT OF <THET1> FOUND. PRINT RESULTS ***
C
3000      WRITE(6,3050)THET1*RD
          WRITE(1,3050)THET1*RD
3050      FORMAT(//' THE MAXIMUM INITIAL SLOPE = 'F6.2' DEGREES')
          WRITE(6,1730)
          WRITE(1,1730)
          WRITE(6,1740)R1,R2,DEL,T,YC,FRIC,SHARP,PTHIK
          WRITE(1,1740)R1,R2,DEL,T,YC,FRIC,SHARP,PTHIK
C
C         *** ENTER A COMMENT TO RESULT FILE <DCPOPT.OUT> IF DESIRED ***
C
3100      WRITE(6,3110)
3110      FORMAT(/' WOULD YOU LIKE TO ENTER A COMMENT TO
         1 THE OUTPUT FILE (Y OR N)? ',$)
          READ(5,400,ERR=3100)REP
          IF(REP.EQ.'N')GOTO 3190
          WRITE(1,3115)
3115      FORMAT(/'     **** NOTES ON PRECEEDING RUN ****'/)
          WRITE(6,3120)
3120      FORMAT(/' ENTER COMMENT ONE LINE AT A TIME,'/'     AND STOP
         1 WITH "S"<RET>')
3125      READ(5,3130)N,LINE(1:N)
3130      FORMAT(Q,80(A,:))
          IF(N.NE.1)GOTO 3140
          IF(LINE(1:1).NE.'S'.AND.LINE(1:1).NE.'s')GOTO 3140
          GOTO 3190
3140      WRITE(1,3150)LINE(1:N)
3150      FORMAT(1X,80(A,:))
          GOTO 3125
3190      WRITE(6,3200)
3200      FORMAT(/' ANOTHER RUN (Y OR N)? ',$)
          READ(5,400,ERR=3190)REP
          IF(REP.EQ.'N')STOP
          I=I+1
          GOTO 100
C
4000      WRITE(6,4100)
          WRITE(1,4100)
4100      FORMAT(/' THET2 WENT TO 30 DEGREES WITH NO SOLUTION.')
          GOTO 3190
          END
```

As an example, using the foregoing program and given a horizontal travel of 1–2 mm, a minimum vertical travel in the steep portion of 1.27 mm, an FR maximum of 2.50, an SH maximum of 0.55 and a plate thickness of 3.6–3.9 mm, a maximum final angle of 71.3° was obtained with a minimum initial angle of 51.0°. For this the radii $R_1$ and $R_2$ of the initial and final positions were 8.00 mm. The total horizontal travel was 1.36 mm, total vertical travel was 2.47 mm, vertical travel in the steep portion was 1.36 mm, FR was 2.05, SH was 0.51 and plate thickness 3.89 mm.

Figure 8:
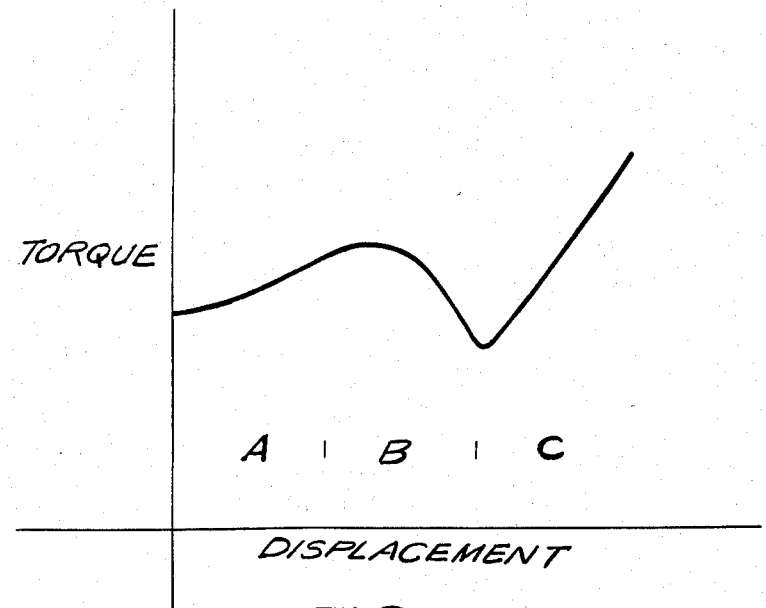
FIG. 8 is a graph of torque vs. displacement for a plate of preferred design according to the invention.

Using a plate so defined, with an Rc of 2 mm, when torque is plotted against displacement, the results are qualitatively shown in FIG. 8. As shown in that figure, the torque decreases sharply as the screw nears the end of the compression stage, and encounters the steep slope indicated at 31 in FIG. 6. When it finally enters the seating phase the sudden increase in torque is easily appreciated by the surgeon who is thus notified in unmistakeable terms that the screw has been seated.

When the invention has been described in terms of a hemispherically shaped screw head, it is obvious that other shapes may be used, requiring only a suitable variation in the shape of the milling tool.

What is claimed is:

1. A compression plate for stabilizing a bone fracture or an osteotomy in compression osteosynthesis, said plate having an upper surface, a lower surface to be placed next to the bone, and at least one elongated hole, the walls of the hole being sloped downwardly, toward the lower surface, and inwardly, and an end wall of the hole having a camming portion curved convexly toward the center of the hole, said camming portion extending from the upper surface to a point adjacent the lower surface.

2. A system for stabilizing a bone fracture or an osteotomy in compression osteosynthesis comprising a plate to be positioned on the bone to be treated, said plate having a lower surface to be placed next to the bone, an upper surface, and at least one elongated hole, and a screw, having a head, for insertion through the hole into a bone section, the walls of the hole being sloped downwardly, toward the lower surface, and inwardly, and an end wall of the hole having a camming portion curved convexly toward the center of the hole, said camming portion extending from the upper surface to a point adjacent the lower surface, and providing a camming surface for said screw head to displace said plate longitudinally as the screw is advanced through the hole.

3. The system claimed in claim 2 whereas the screw has a hemispherical head.

4. A compression plate for stabilizing a bone fracture or an osteotomy in compression osteosynthesis, said plate having a lower surface to be placed next to the bone and an upper surface, and at least one elongated hole for receiving a screw, having a head, to be advanced into the bone, the walls of said hole being sloped downwardly toward the lower surface of the plate, and inwardly, to provide a camming surface for a screw head to move the plate longitudinally when the screw is advanced into the hole, said camming surface having a first section having a slope, measured with respect to the plane of said plate, such as to require an increasing torque as the screw is advanced in contact with said first section into the hole, a second section, having a greater slope than said first section, requiring diminishing torque and a third section having a slope less than the slope of said first section, thus requiring sharply increasing torque as said screw is seated in the hole.

5. A system for stabilizing a bone fracture or an osteotomy in compression osteosynthesis which comprises a plate to be positioned on the bone to be treated, said plate having a lower surface to be placed next to the bone, an upper surface, and at least one elongated hole; and a screw having a head, for insertion in the hole, the walls of said hole being sloped toward the lower surface of the plate, and inwardly, to provide a camming surface for said screw head to displace said plate longitudinally as said screw is advanced into the hole, said camming surface having a first portion having a slope, measured with respect to the plane of said plate, such as to require an increasing torque as said screw is advanced through the hole in contact with said first portion, a second section having a greater slope than said first section such as to require a diminishing torque, and a third section having a slope less than the slope of said first section to require a sharply increased torque as said screw is seated in said hole.

6. The system claimed in claim 5 wherein the screw has a hemispherical head.

7. A compression plate for stabilizing a bone fracture or an osteotomy in compression osteosynthesis, said plate having an upper surface, a lower surface to be placed next to the bone, and at least one oval elongated hole, the walls of the hole being sloped inwardly from the upper surface toward the lower surface and an end wall of the hole having an upper inclined camming portion of substantially constant slope, as defined by the angle between the wall and the plane of the upper surface of the plate, a lower camming portion of substantially constant slope greater than the slope of said upper section and a curved intermediate section between said upper and lower sections.

8. The plate claimed in claim 7 wherein the intermediate section is shaped to the arc of a circle.

9. A compression plate for stabilizing a bone fracture or an osteotomy in compression osteosynthesis, said plate having a lower surface to be placed next to the bone, and an upper surface, and at least one oval elongated hole for receiving a screw to be advanced into the bone, the wall of said hole being being sloped from the upper surface of the plate inwardly toward the lower surface to provide a camming surface for a screw to move the plate longitudinally as the screw is advanced into the hole, an end wall of the hole having a first, upper camming portion having a substantially constant slope, as defined by the angle between the end wall and the upper surface of the plate, such as to require an increasing torque as the screw is advanced in contact with said upper portion, a second lower portion having a substantially constant slope, greater than the slope of said upper portion, requiring diminishing torque as said screw is advanced, and a third portion having a slope less than the slope of said first portion corresponding to the seating of said screw in said hole, requiring sharply increased torque.

* * * * *

UNITED STATES PATENT AND TRADEMARK OFFICE
CERTIFICATE OF CORRECTION

PATENT NO. : 4,513,744
DATED : April 30, 1985
INVENTOR(S) : Kaj Klaue

It is certified that error appears in the above—identified patent and that said Letters Patent is hereby corrected as shown below:

Column 3, line 10, "and $(X_2, X_2)$ may coincide" should be

--and $(X_2, Y_2)$ may coincide--

Column 14, line 47, "said hole being being sloped" should be

--said hole being sloped--

Signed and Sealed this

Nineteenth Day of November 1985

[SEAL]

Attest:

DONALD J. QUIGG

Attesting Officer    Commissioner of Patents and Trademarks